United States Patent
Frach et al.

(10) Patent No.: US 7,807,981 B2
(45) Date of Patent: Oct. 5, 2010

(54) DATA PROCESSING DEVICE, TOMOGRAPHY APPARATUS FOR EXAMINATION OF AN OBJECT OF INTEREST, METHOD OF EXAMINING AN OBJECT OF INTEREST, COMPUTER-READABLE MEDIUM AND PROGRAM ELEMENT

(75) Inventors: Thomas Frach, Aachen (DE); Gereon Vogtmeier, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 278 days.

(21) Appl. No.: 12/067,182

(22) PCT Filed: Sep. 12, 2006

(86) PCT No.: PCT/IB2006/053225
§ 371 (c)(1),
(2), (4) Date: Mar. 18, 2008

(87) PCT Pub. No.: WO2007/034357
PCT Pub. Date: Mar. 29, 2007

(65) Prior Publication Data
US 2008/0272296 A1    Nov. 6, 2008

(30) Foreign Application Priority Data
Sep. 22, 2005    (EP)    ................ 05108742

(51) Int. Cl.
*A61N 5/00*    (2006.01)
*G21G 5/00*    (2006.01)

(52) U.S. Cl. .................. 250/492.1; 250/306; 250/374; 250/385.1; 250/207; 378/5; 378/6; 378/7; 378/8; 378/15; 378/20; 375/259; 375/295; 375/296

(58) Field of Classification Search .............. 250/492.1, 250/306, 374, 385.1, 207; 378/5–8, 15, 20; 375/259, 295, 296
See application file for complete search history.

(56) References Cited

U.S. PATENT DOCUMENTS

| 5,577,026 | A | 11/1996 | Gordon et al. |
| 6,067,342 | A | 5/2000 | Gordon |
| 2003/0185310 | A1 * | 10/2003 | Ketchum et al. ............ 375/259 |

FOREIGN PATENT DOCUMENTS
WO    03053246 A1    7/2003

OTHER PUBLICATIONS

Herdin, M., et al.; The influence of channel models on simulated MIMO performance; 2004; IEEE; 4 pages.

* cited by examiner

*Primary Examiner*—Jack I Berman
*Assistant Examiner*—Meenakshi S Sahu (57) ABSTRACT

A data processing device, comprising a plurality of emitter antennas arranged on a movable data acquisition device and adapted to emit electromagnetic radiation including data acquired by the movable data acquisition device, a plurality of receiver antennas each adapted to receive the electromagnetic radiation emitted by each of the plurality of emitter antennas, and a data processing unit coupled to the plurality of receiver antennas and adapted to extract the data acquired by the movable data acquisition device from the electromagnetic radiation received by the plurality of receiver antennas.

23 Claims, 3 Drawing Sheets

DATA PROCESSING DEVICE, TOMOGRAPHY APPARATUS FOR EXAMINATION OF AN OBJECT OF INTEREST, METHOD OF EXAMINING AN OBJECT OF INTEREST, COMPUTER-READABLE MEDIUM AND PROGRAM ELEMENT

The invention relates to the field of data transmission. In particular, the invention relates to a data processing device, to a tomography apparatus for examination of an object of interest, to a method of examining an object of interest, to a computer-readable medium and to a program element.

Over the past several years, X-ray baggage inspections have evolved from simple X-ray imaging systems that were completely dependent on an interaction by an operator to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector. The X-ray radiation source and the detector may be mounted on a rotating gantry and may rotate around an item of baggage under investigation, e.g. in a helical manner. The data then have to be transferred from the rotating detector to a static data processing device for evaluating the data to reconstruct the 3D structure of the baggage item.

Computed tomography (CT) is thus a process of using digital processing to generate a three-dimensional image of the internals of an object from a series of two-dimensional X-ray images taken around a single axis of rotation. The reconstruction of CT images can be done by applying appropriate algorithms.

Data acquired by a computer tomography scanner may produce large amounts of real time data that need to be transferred from the rotating detector to a stationary part of a gantry. The bandwidth requirements of computer tomography scanners become larger and larger, for instance several Gigabits per second.

In a conventional solution, a mechanical or optical slip ring system may be implemented, in which the data is transferred from the rotating part of the gantry to the static part of the gantry by means of a mechanical slip ring or an optical slip ring. Such a system may be prone to performance degradation through wearout and contamination.

Wireless systems, on the other hand, do not suffer from these problems. However, using a conventional wireless system, the propagation environment starts to play a prominent role. As the propagation environment found in a rotating gantry is non-stationary and strong multipath, conventional antenna based systems will likely fail to provide the required bandwidth.

WO 03/053246A1 of the same applicant Philips discloses a data acquisition system for a computer tomography scanner, wherein signals generated by detectors are transferred to a data acquisition system mounted on a rotor that processes the signals to generate digital data therefrom. The data acquisition system routes, responsive to an appropriate routing algorithm, portions of the digital data that it generates to each of at least one transmitter. Each of the at least one transmitter transmits the data that it receives as data signals to at least one receiver. Thus, a plurality of parallel transmission channels are used in order to improve bandwidth.

However, with increasing bandwidth requirements of modern computed tomography scanners, even this wireless data transmission may not be sufficient.

There may be a need for a data processing system providing a sufficient bandwidth.

This may be achieved by a data processing device, by a tomography apparatus for examination of an object of interest, by a method of examining an object of interest, by a computer-readable medium and by a program element with the features according to the independent claims.

According to an exemplary embodiment of the invention, a data processing device is provided, comprising a plurality of emitter antennas arranged on a movable data acquisition device and adapted to emit electromagnetic radiation including (or encoding) data acquired by the movable data acquisition device, a plurality of receiver antennas each adapted to receive the electromagnetic radiation emitted by each of the plurality of emitter antennas, and a data processing unit coupled to the plurality of receiver antennas and adapted to extract the data acquired by the movable data acquisition device from the electromagnetic radiation received by the plurality of receiver antennas.

According to another exemplary embodiment of the invention, a tomography apparatus for examination of an object of interest is provided, the tomography apparatus comprising an electromagnetic radiation source adapted to emit a beam to the object of interest, at least one detecting device adapted to detect the beam after being transmitted through the object of interest, and a data processing device having the above-mentioned features and being adapted to determine structural information concerning the object of interest based on an analysis of detecting signals received from the at least one detecting device coupled to the plurality of emitter antennas of the data processing device.

According to still another exemplary embodiment of the invention, a method of processing data is provided, the method comprising emitting, by means of a plurality of emitter antennas arranged on a movable data acquisition device, electromagnetic radiation including data acquired by the movable data acquisition device, receiving, by means of a plurality of receiver antennas, the electromagnetic radiation emitted by each of the plurality of emitter antennas, and extracting, by means of a data processing unit coupled to the plurality of receiver antennas, the data acquired by the movable data acquisition device from the electromagnetic radiation received by the plurality of receiver antennas.

According to yet another exemplary embodiment of the invention, a computer-readable medium is provided, in which a computer program of processing data is stored which, when being executed by a processor, is adapted to control or carry out the above mentioned method.

According to still another exemplary embodiment of the invention, a computer-readable medium is provided, in which a computer program of processing data is stored which, when being executed by a processor, is adapted to control or carry out the above mentioned method.

According to yet another exemplary embodiment of the invention, a data processing device is provided, comprising a plurality of emitter antennas adapted to emit electromagnetic radiation in which data are encoded, a plurality of receiver antennas each adapted to receive the electromagnetic radiation emitted by each of the plurality of emitter antennas, wherein the plurality of receiver antennas are arranged on a movable device, and a data processing unit coupled to the plurality of receiver antennas and adapted to extract the data from the electromagnetic radiation received by the plurality of receiver antennas.

Embodiments of the invention can be realized using one or more special electronic optimization circuits, i.e. in hardware, or in hybrid form, i.e. by means of software components and hardware components. The computer-readable medium and the program element may be implemented in a control system for controlling a data processing system.

According to an exemplary embodiment of the invention, a system of a movable data acquisition device having attached thereto multiple emitter antennas and a plurality of receiver antennas (which do not necessarily have to be provided on the movable data acquisition device) is provided, wherein each of the emitter antennas emits data signals, and all signals emitted by a particular one of the emitter antennas is received by all or a plurality of the receiver antennas. Thus, the signal emitted by each of the emitter antennas is received by multiple receiver antennas. Then, these (for instance at least partially redundant) data fragments are supplied to a data processing unit which may compose the individual fragments so as to reconstruct the original data set in an efficient manner so that a high bandwidth of data may be obtained.

Such a system having N emitter antennas (which may also be denoted as sender antennas or transmitter antennas) and which has M receiver antennas (which may also be denoted as detector antennas) may for instance evaluate up to N×M signal fragments. The data communication scheme introduced with such a data transmission system may enable the data processing unit to retrieve all required data in an efficient manner.

Such a system may be designed as a MIMO system ("Multiple-Input Multiple-Output") which is well known as such by a skilled person and which may be implemented for wireless data transfers from/to the detector in a rotating part of the data processing device which may be, for instance, part of a medical tomography/scanning system. The antennas may be located on the rotating and/or on the static part of the equipment. According to an exemplary embodiment, a MIMO-based slip ring communication system may thus be provided.

MIMO stands for "Multiple-Input Multiple-Output", which relates to an abstract mathematical model for data recovery from a plurality of data fragments. Particular in radio communications, if multiple antennas are employed, MIMO exploits phenomena such as multipath propagation to increase throughput and/or to reduce bit error rates. Channel capacity (a theoretical measure of throughput) for a MIMO system may be increased as the number of antennas are increased, proportional to the minimum of number of transmit and receive antennas.

MIMO may benefit of multiplexing to increase wireless bandwidth and/or range. According to MIMO algorithms, information is sent out over two or more antennas and the information is received via multiple antennas as well. MIMO may use additional pathways to transmit more information and may then recombine the signal on the receiving end. Thus, the MIMO system may provide a significant capacity gain over conventional single antenna systems, along with more reliable communication.

Such a MIMO system may have multiple antennas. It may take advantage of multipath effects, where a transmitted signal arrives at the receiver through a number of different paths. Each path can have a different time delay, and the result is that multiple instances of a single transmitted symbol arrive at the receiver at different times.

Conventionally, multipath is a source of interference, but a MIMO system according to an exemplary embodiment may use the fact that data will arrive at the receivers at different times through different paths to improve the quality of the data link. For example, rather than relying on a single antenna path to receive the entire message, the message can be pieced together based on fragments received by the various antennas. This can act to increase the data rate at a given range and/or to increase system range for a given data rate.

Further explanation and particularly examples for MIMO algorithms which may be implemented in the system according to an embodiment of the invention is given, for instance in Ernst Bonek, "MIMO and its Radio Channel Modeling", CCCD Lund, Sep. 27, 2004 and is available via http://www.nt.tuwien.ac.at/mobile/research/mimo/mimo.pdf. The various MIMO algorithms described in this document are explicitly included in the disclosure of this application, and a system according to an exemplary embodiment of the invention may be operated using one of these algorithms.

A MIMO system may be defined as comprising several antenna elements, plus adaptive signal processing, at both transmitter and receiver, wherein the combination of both may exploit the spatial dimension of a transmission channel. By means of MIMO, several replicas of transmitted signals may be used, and the entire bandwidth may be improved.

According to an exemplary embodiment, a Multiple-Input Multiple-Output (MIMO) communication system is provided to achieve a high bandwidth, wireless data transfer and slip ring based systems, for instance Computed Tomography (CT), Positron Emission Tomography (PET) or Single Photon Emission Computed Tomography (SPECT) systems. MIMO systems may comprise N×M antennas can take advantage of the multipath propagation environment found in the closed gantry and, possibly, in the surrounding lab environment to provide high communication bandwidth through frequency reuse. Since MIMO systems are already beginning to enter the WLAN ("Wireless Local Area Network") market, cheap integrated solutions with sufficient communication bandwidth are enabled.

According to an exemplary embodiment, a Multiple-Input Multiple-Output (MIMO) wireless communication system is used for data transfers from/to the detector in a rotating gantry. MIMO systems with N×M antennas are capable of increasing the total communication bandwidth through the reuse of frequencies in a non-stationary multipath environment. When MIMO systems are implemented for wireless LAN communications, the communication subsystem could make use of cheap chip sets to provide cost efficient solution to the data transfer task.

The increase in spectral efficiency offered by a MIMO system (which, according to an embodiment of the invention, is used for transmitting data between a moved and a static system) is based on the utilization of space (or antenna) diversity at both the transmitter and the receiver. With a MIMO system, the data stream may be demultiplexed into $n_T$ separate sub-streams. The number $n_T$ may equal the number of transmit antennas. Each sub-stream may then be encoded into channel symbols. It is possible to impose the same data rate on all transmitters, but adaptive modulation rate can also be utilized on each of the sub-streams. The signals are received by $n_R$ receiver antennas. With this transmission scheme, there may be a significant increase in spectral efficiency. The high spectral efficiencies attained by a MIMO system are enabled by the fact that in a rich scattering environment, the signals from each individual transmitter appear highly uncorrelated at each of the receive antennas. When the signals are conveyed through uncorrelated channels between the transmitter and receiver, the signals corresponding to each of the individual transmit antennas have attained different spatial signatures. It is possible to reconstruct all the input sequences at the output with negligible probability of error. A measure of how much information that can be transmitted and received with a negligible probability of error may be denoted as the channel capacity.

In a MIMO system, estimation of the transmission medium may be implemented. Signals may be processed so as to retrieve data encoded therein, and signal distortions may be removed by mathematically evaluating the individually received signal fragments. In the context of a MIMO communication system, data may be transmitted from emitters and received by receivers. Then, the receivers may send back a feedback signal to the emitters which the emitters may receive and evaluate. The communication path may be defined by the propagation environment. An estimated propagation environment (provided by the receiver), can be used by the transmitter to do pre-emphasis on the transmitted data. They can also be used to adapt the amount of redundant data in the data stream to the current propagation environment.

In such a MIMO system, the properties of sending data may be selectively adjusted between the bidirectionally coupled emitter and receiver antennas. For instance, (spatial) emission characteristics may be adjusted so as to obtain a high quality transmission. Mathematically, a transmission matrix may be adjusted, which transmission matrix may describe transmission properties between emitter and receiver antennas. When one of the emitter antennas emits a signal, all receiver antennas may "listen" to this signal simultaneously.

For estimating the communication channel, it is possible that the emitters send a training signal which is known by the receivers. The receivers may then derive information about the communication path based on a comparison of the pre-known information and of the received information.

All emitters of a MIMO system may send on the same (carrier) frequency, or the emitters of a MIMO system may send on different (carrier) frequencies.

The data transmitted by means of the data signals emitted by the emitters and received by the receivers may be (partly) redundant when a high bit rate or quality of service is desired, or may be free of any redundancy when a high bandwidth is desired.

According to an exemplary embodiment, a wireless system for high bandwidth transmission based on a multi channel method may be provided, particularly based on a MIMO system.

Exemplary fields of application are any systems requiring high bandwidth data link between a moving data source and a stationary data processing hardware, or vice versa. The system according to an embodiment of the invention could be applied in CT scanners, but also in SPECT scanners and PET scanners using rotation or wobbling to achieve uniform sampling of the object space. Moreover, the solution provides a standardized and cheap data communication interface between the scanner and the data processing host.

According to an exemplary embodiment of the invention, the MIMO technique is applied to the data transmission between a rotating gantry and a stationary workstation.

In such a configuration or arrangement, a periodically repeated transmission channel may result. This can be used to significantly reduce the overhead of the necessary channel estimation of the MIMO system.

According to an exemplary embodiment of the invention, the described method may be implemented as a technical method for medical applications.

Embodiments of the invention may have the advantage in comparison to conventional wireless solutions that the adaptive adjustment feature may improve the quality of the system in the presence of distortions which may originate from X-rays, high voltage, etc. The adaptive adjustment to the channel properties together with CDMA ("Code Division Multiple Access") or an adaptive performance by FEC ("Forward Error Correction") may further improve the reliability of the system.

Beyond this, with a combined modality like PET/CT, the same base station may be used for both devices (sequentially or even simultaneously, when sufficient bandwidth is available). Taking this measure may further reduce costs.

Next, further exemplary embodiments of the invention will be described.

In the following, exemplary embodiments of the data processing devices will be described. However, these embodiments also apply to the tomography apparatus, for the method of processing data, for the computer-readable medium and for the program element.

The movable data acquisition device may be a rotatable data acquisition device. For instance, the movable data acquisition device may be rotating part of a gantry which may be used in the context of a tomography apparatus. Such a gantry has mounted thereon a radiation source and a radiation detector and rotates around an object under investigation, for instance an item of baggage to be inspected or a patient under investigation. According to the data processing device of an embodiment of the invention, the emitter antennas may also be arranged in a rotatable manner on the rotating gantry, whereas the receiver antennas and/or the data processing unit may not necessarily be mounted on the rotatable gantry.

The number of emitter antennas may be larger, equal or smaller than the number of receiver antennas and may be, for instance, two, three, four, five, six, or even larger. It is not necessary that the number of emitter antenna equals to the number of receiver antennas.

The plurality of an emitter antennas, the plurality of receiver antennas and the data processing unit may be adapted as a Multiple-Input Multiple-Output (MIMO) communication system. By taking this measure, the bandwidth of the data transfer from the emitter antennas to the receiver antennas, or vice versa, can be increased, since the data items received by the receiver antenna may be processed together and may be used to reconstruct the original data set. By using a suitable MIMO algorithm, the bandwidth of the system can be significantly increased.

The data to be transmitted from the emitter antennas to the receiver antennas may be transmitted by means of modulation of data encoding signals on a carrier wave. The plurality of receiver antennas may be adapted for a wireless communication with the plurality of emitter antennas. Such a wireless communication may be realized by means of an exchange of electromagnetic radiation, for instance in the radio frequency domain, in the microwave domain, in the optical domain, in the infrared domain or in the ultraviolet domain.

A communication in the optical domain may be quite challenging as the optical receivers should be very small and it might be appropriate to detect the phase of the signal simultaneously. On the other hand, optical links may provide even more bandwidth than MIMO using line-of-sight communications without any multipath components.

At least a part of the plurality of receiver antennas may be arranged spatially fixed and apart from the movable data acquisition device. By taking this measure, it is possible to transfer data from a rotating or movable system to a spatially fixed system, for instance an evaluation computer which may be coupled with a graphical user interface for interaction with a human user.

At least a part of the plurality of receiver antennas may be arranged on the movable data acquisition device. In such a scenario, the data processing device may be coupled to the plurality of receiver antennas by means of a wired communication channel. Such a wired communication channel may include the transmission of data by means of an electric signal, for instance an electric current or an electric voltage or by an optical connection, for instance using glass fibres for transferring a plurality of data in a fast manner.

Furthermore, the data processing unit may be arranged spatially fixed and apart from the movable data acquisition device. Thus, the data processing (and the image reconstruction located further downstream) may be spatially separated from the image data acquisition. The data transfer from the rotating system to the spatially fixed or static system may thus be realized without a mechanical slip ring. This may simplify and accelerate the data transfer and may increases the lifetime of such a system since a wireless communication is less prone to performance degradation through wearout. The data processing device may comprise a shielding element for (electromagnetically) shielding the movable data acquisition device with respect to the data processing unit and/or an environment. In the context of a data acquisition system, for instance a CT system, harmful electromagnetic radiation, for instance in the X-ray domain, may occur. Thus, the shielding element may be provided to shield such harmful radiation against the environment. Additionally or alternatively, the shielding may be implemented to reduce electromagnetic interference (EMI) of the MIMO system to the surrounding medical devices. If EMI is of concern, the MIMO can be built-in close to the gantry and the whole configuration could be shielded to the outside. An X-ray window might be needed, and this is typically made of metal. Such a shielding element may be arranged in a manner to avoid that, by means of the shielding element, the leaking of electromagnetic radiation is reduced.

The plurality of receiver antennas may be adapted to emit electromagnetic radiation including feedback information concerning the communication between the plurality of receiver antennas and the plurality of emitter antennas, wherein the plurality of emitter antennas may be adapted to receive the electromagnetic radiation emitted by the plurality of receiver antennas.

The transmission path for data to be transmitted from the movable device (e.g. scanner) to the workstation may also be denoted as "downlink" direction, and the term "uplink" may be used for the other transmission direction, i.e. from the workstation to the movable device.

Also, it is mentioned that the data communication according to an exemplary embodiment may be asymmetric (low bit rate up, high bit rate down).

Thus, the property "emitter" antenna refers to the emission of data signals. Similarly, the property "receiver" antenna refers to the reception of data signals. However, apart from the exchange of data messages between the emitter antennas and the receiver antennas, the receiver antennas may also send feedback signals to the emitter antennas. Such a feedback may be advantageous since it may allow that the communication properties are controlled and, if desired, adjusted between the emitter antennas and the receiver antennas. For this purpose, it may be necessary to process the feedback data. Such a bidirectional communication may also be performed in the context of signal estimation or channel matrix estimation in the context of a MIMO communication system.

Thus, a communication between the plurality of receiver antennas and the plurality of emitter antennas may be bidirectional. In other words, the emitter antenna may also serve as a receiver antenna, and vice versa.

A communication between the plurality of receiver antennas and the plurality of emitter antennas may include estimating properties of a transmission medium used for the data transfer communication. In the context of a MIMO system, a high bandwidth capability may be obtained when an appropriate communication path is established. The estimation of properties of a transmission medium may serve to adjust the communication path so that the data amount to be transmitted can be made large.

A communication between the plurality of receiver antennas and the plurality of emitter antennas may include at least one of the group consisting of estimating a channel matrix, estimating a channel distortion, and estimating a channel equalization. This embodiment may be implemented in a scenario in which the plurality of receiver antennas and the plurality of emitter antennas form part of a MIMO system. In this case, an adaptation or optimization of a channel matrix describing the communication properties between emitter antennas and receiver antennas may be suitable to obtain a sufficiently high bandwidth.

The data processing device may be configured as one of the group consisting of a baggage inspection apparatus, a medical application apparatus, a material testing apparatus and a material science analysis apparatus. Also a material testing apparatus may be provided. However, the data processing device is not restricted to the described applications, any other application may be used as well.

Next, exemplary embodiments of the tomography apparatus will be described. However, these embodiments also hold for the data processing devices, for the method of processing data, for the computer-readable medium and for the program element.

The tomography apparatus may be adapted as one of the group consisting of a Computed Tomography apparatus (CT), a Positron Emission Tomography apparatus (PET), and a Single Photon Emission Computed Tomography apparatus (SPECT).

Computed Tomography (CT) is a medical imaging method employing tomography where digital processing is used to generate a three-dimensional image of the internals of an object from a large series of two-dimensional X-ray images taken around a single axis of rotation. CT is not only used in healthcare, but also in other fields, for instance non-destructive materials testing or baggage inspection. Other exemplary use fields are cranial CT, chest CT, cardiac CT and abdominal and pelvic CT.

Positron Emission Tomography (PET) is a nuclear medicine medical imaging technique which produces a three-dimensional image or map of functional processes in the body. In the context of a PET examination, a short-lived radioactive tracer isotope which decays by emitting a positron, chemically combined with a metabolically active molecule, is injected into a subject (for instance into blood circulation). Then, the subject is placed in the imaging scanner. The short-lived isotope decays, emitting a positron. After travelling up to a few mm, the positron annihilates with an electron, producing a pair of gamma ray photons moving in opposite directions. These are detected when they reach a scintillator material in the scanning device, creating a burst of light which may be detected by photomultiplier tubes. By measuring such radiation, a position of the tracer isotope in the body can be plotted, allowing the chemical uptake or cavity of certain parts of the body to be determined.

Single Photon Emission Computed Tomography (SPECT) is a nuclear medicine tomographic imaging technique using gamma rays. The technique results in a set of image slices to a patient, showing the distribution of a radiopharmaceutical. First, the object is injected with a gamma emitting radiopharmaceutical. Then a series of projection images are acquired using a gamma camera. The acquisition involves the gamma camera rotating around the patient acquiring images at various positions. The number of images and the rotation angle covered varies depending on the type of investigation required. The projection images are stored digitally and a sophisticated computer program may be used to process them and produces slices, this process is called reconstruction.

The movable data acquisition device of the tomography apparatus may comprise a rotatable gantry on which the electromagnetic radiation source (an X-ray tube), the at least one detecting device (single-slice detector or multi-slice detector) and the plurality of emitter antennas are mounted. By this geometrical configuration, a high bandwidth tomography apparatus with sophisticated image quality may be obtained.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustration in the drawings is schematically. In different drawings, similar or identical elements are provided with the same reference signs.

Figure 1:
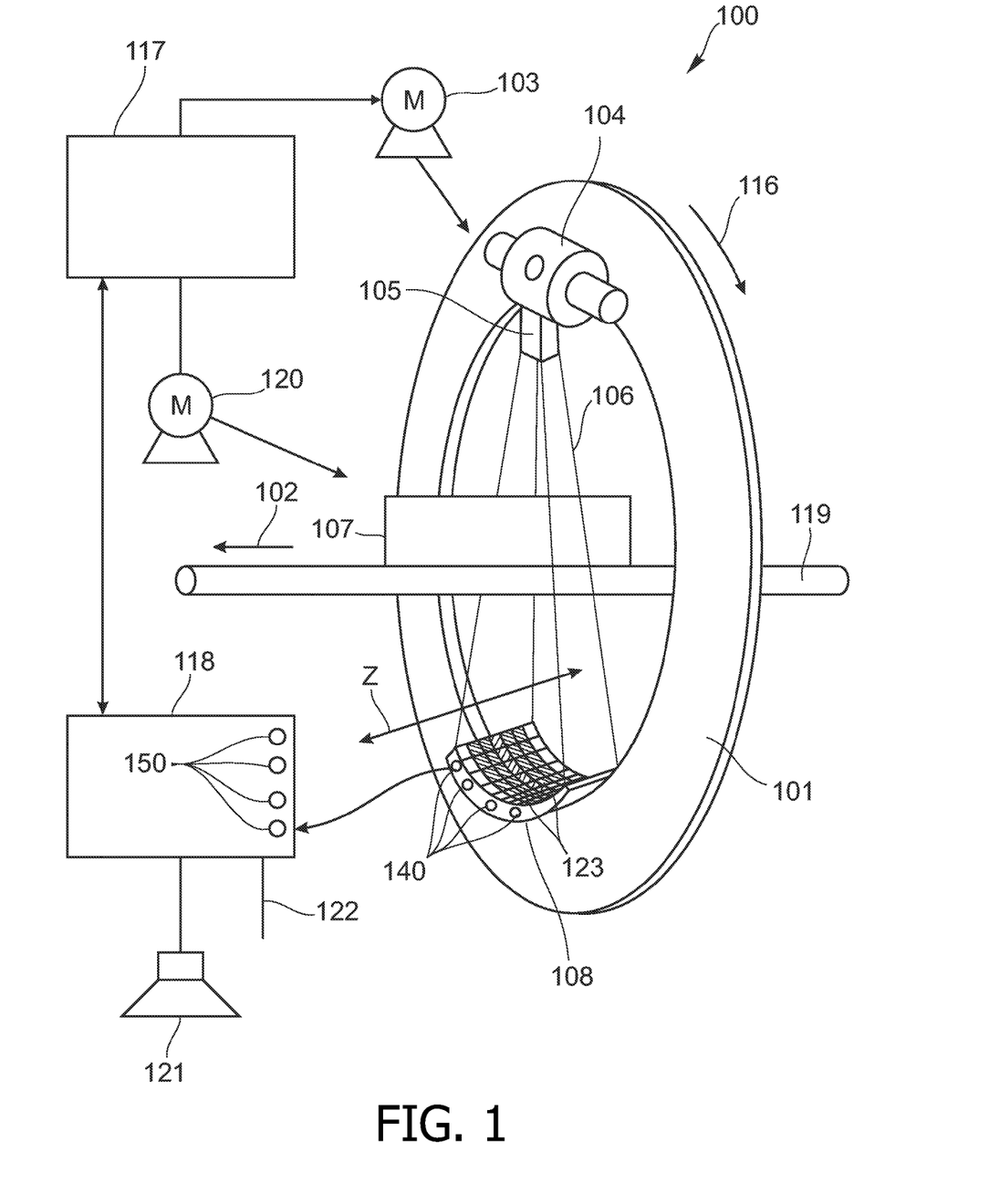
FIG. 1 shows a computed tomography apparatus according to a first embodiment of the invention.

FIG. 1 shows an exemplary embodiment of a computed tomography scanner system according to the present invention.

With reference to this exemplary embodiment, the present invention will be described for the application in baggage inspection to detect hazardous materials, such as explosives, in items of baggage. However, it should be noted that the present invention is not limited to this application, but may also be applied in the field of medical imaging (particularly medical CT), or other industrial applications such as material testing.

The computer tomography apparatus 100 depicted in FIG. 1 is a cone-beam CT scanner. However, the invention may also be carried out with a fan-beam geometry. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an embodiment of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the cone beam 106. The detector 108 depicted in FIG. 1 comprises a plurality of detector elements 123 each capable of detecting, in an energy-resolving manner or in a non-energy-resolving manner, X-rays which have been scattered by the object of interest 107.

During a scan of the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a data processing or determination unit 118.

In FIG. 1, the object of interest 107 is an item of baggage which is disposed on a conveyor belt 119. During the scan of the object of interest 107, while the gantry 101 rotates around the item of baggage 107, the conveyor belt 119 may or may not displace the object of interest 107 along a direction parallel to the rotational axis 102 of the gantry 101. By this, the object of interest 107 is scanned along a circular scan path (when the conveyor belt 119 does not displace the object of interest 107) or along a helical scan path (when the conveyor belt 119 does displace the object of interest 107). The conveyor belt 119 may be stationary or may move and may also be stopped during the scans to thereby measure signal slices. Instead of providing a conveyor belt 119, for example in medical applications where the object of interest 107 is a patient, a moveable table is used. However, it should be noted that in all of the described cases it is also possible to perform a helical scan, where there is a displacement in a direction parallel to the rotational axis 102, and additionally the rotation of the gantry 101 around the rotational axis 102. Alternatively, in all of the described cases it is also possible to perform a circular scan, where there is no displacement in a direction parallel to the rotational axis 102, but only the rotation of the gantry 101 around the rotational axis 102.

Further, it shall be mentioned that, as an alternative to the cone-beam configuration shown in FIG. 1, the invention can be realized by a fan-beam configuration. In order to generate a primary fan-beam, the aperture system 105 can be configured as a slit collimator.

The detector 108 is coupled to the determination unit 118 in a manner as will be described below in further detail. The determination unit 118 receives the detection result, i.e. the read-outs from the detector elements 123 of the detector 108 and determines a scanning result on the basis of these read-outs. Furthermore, the determination unit 118 communicates with the motor control unit 117 in order to coordinate the movement of the gantry 101 with motors 103 and 120 with the conveyor belt 119.

The determination unit 118 is adapted for reconstructing an image from read-outs of the detector 108. A reconstructed image generated by the calculation unit 118 may be output to a display (not shown in FIG. 1) via an interface 122.

The determination unit 118 may be realized by a data processor to process read-outs from the detector elements 123 of the detector 108.

Furthermore, as may be taken from FIG. 1, the determination unit 118 may be connected to a loudspeaker 121, for example to automatically output an alarm in case of the detection of suspicious material in the item of baggage 107.

The computed tomography apparatus 100 for examination of the object of interest 107 includes the detector 108 having the plurality of detecting elements 123 arranged in a matrix-like manner, each being adapted to detect X-rays passing through the object of interest 107. Further, the computed tomography apparatus 100 comprises the determination unit 118 adapted to determine structural information concerning the object of interest 107 based on an analysis of detecting signals received from the detecting elements 123.

The computed tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. Alternatively, not shown in FIG. 1, a slit collimator can be used instead of collimator 105 to produce a fan-beam. The detecting elements 123 form a multi-slice detector array 108. The computed tomography apparatus 100 is configured as a baggage inspection apparatus.

In the following, a data processing device of the computed tomography apparatus 100 will be described in detail.

This data processing device comprises a plurality of emitter antennas 140 which are arranged on the detector 108 and which are adapted to emit radio frequency radiation having encoded the data acquired by the detector 108. For instance, the data may be modulated on a carrier signal. The emitter antennas 140 communicates in a wireless manner with a plurality of receiver antennas 150 which receive the radio waves emitted by the emitter antennas 140. Particularly, each of the receiver antennas 150 receives the radiation emitted by each of the emitter antennas 140.

The determination unit 118 is coupled to the receiver antennas 150 and is adapted to extract the data acquired by the detector 108 from the electromagnetic radiation received by the receiver antenna 150 according to the MIMO principle.

As indicated in FIG. 1, the number of emitter antennas 140 equals to the number of receiver antenna 150 and is four. However, the number of the emitter antennas 140 can also be larger or smaller than the number of the receiver antennas 150. The emitter antennas 140 and the receiver antennas 150 form a Multiple-Input Multiple-Output (MIMO) communication system.

The receiver antennas 150 are spatially fixed on the determination unit 118 and are located apart from the rotating gantry 101. According to FIG. 1, the movable data acquisition system comprises the rotatable gantry 101 on which the electromagnetic radiation source 104, the detector 108 and the emitter antennas 140 are mounted to rotate with the gantry 101.

By means of the wireless MIMO communication system of FIG. 1, a high band-width together with a non-contact data transmission system for transmitting data from a rotating system to a spatially fixed system, or vice versa, is enabled.

It is also possible that the receiver antennas 150 send back feedback signals to the emitter antennas 140. Based on these feedback signals, it is possible to adjust or optimize the the receiver antennas 150 and the emitter antennas 140. For this purpose, computational resources may be provided coupled to the emitter antennas 140 so that the emission characteristics of the emitter antennas 140 may be adjusted, if necessary.

Figure 2:
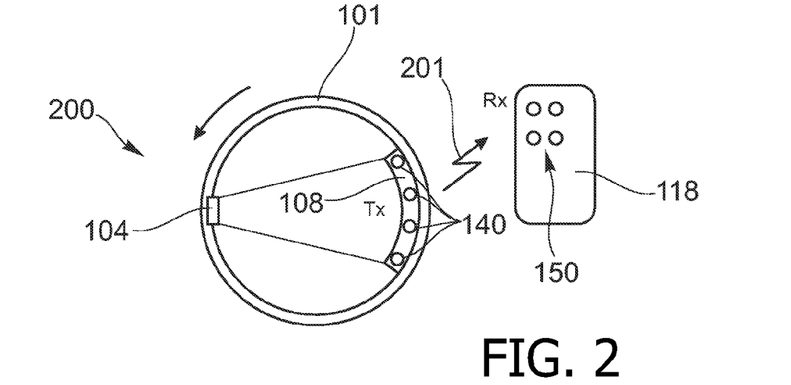
FIG. 2 shows a computed tomography apparatus according to a second embodiment of the invention.

In the following, referring to FIG. 2, a computed tomography apparatus 200 according to an exemplary embodiment of the invention will be described.

The computed tomography apparatus 200 is adapted for wireless communication 201 between the emitter antennas 140 and the receiver antennas 150. Referring to FIG. 2, a commercially available MIMO system with sufficient bandwidth implemented on a computed tomography apparatus 200 is particularly installed on the detector 108 and in the reconstruction workstation 118.

The gantry 101 is partially free from a metallic cover so as to allow free propagation of the outside. Hence, there is a propagation path between the emitter antennas 140 and the receiver antennas 150, but MIMO can deal with reflections on the housing.

In the following, referring to FIG. 3, a computed tomography apparatus 300 according to an exemplary embodiment of the invention will be described.

Figure 3:
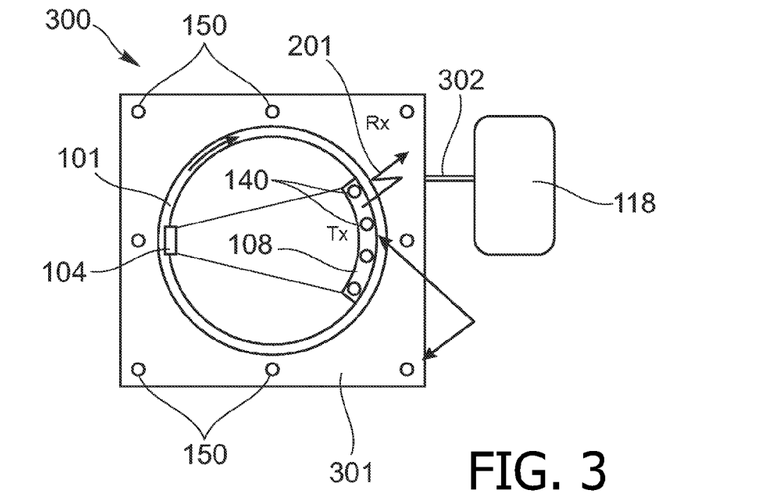
FIG. 3 shows a computed tomography apparatus according to a third embodiment of the invention.

In the scenario of FIG. 3, the gantry comprises the rotating part 101 and a static part 301. The receiver antennas 150 are provided on the static part 301 of the gantry. The emitter antennas 140 are provided on the rotating part 101 of the gantry. A wireless communication 201 is enabled between the emitter antennas 140 and the receiver antennas 150. The receiver antennas 150 communicate via a wired communication channel 302 with the workstation 118. Thus, FIG. 3 shows a shielded MIMO communication system.

In the case of FIG. 3, an implementation is shown which restricts the data linked to the shielded gantry 101, 301. This implementation may suppress electromagnetic interference (EMI) outside of the scanner gantry. Due to the short range, low transmission power is needed to communicate inside the gantry 101, 301. Also, usage of a suitable frequency band (for instance 60 GHz, where oxygen resonance leads to high attenuation) might help keeping the electromagnetic interference low. The receiver antennas 150 are placed inside of the gantry 101, 301, particularly coupled to the static part of the gantry 301, and a high bandwidth connection 302 (e.g. cable, optical communication path, etc.) may be used to couple the signals to the outside workstation 118.

In the following, referring to FIG. 4, a computer tomography system 400 according to an exemplary embodiment of the invention will be described.

Figure 4:
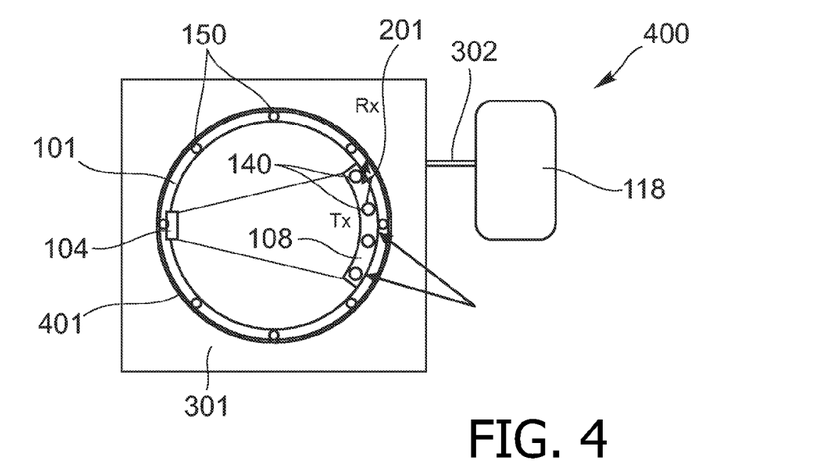
FIG. 4 shows a computed tomography apparatus according to a forth embodiment of the invention.

As shown in FIG. 4, this implementation restricts the wave propagation to a shielding waveguide 401 since the closed waveguide 401 may avoid any possible EMI problems inside the scanner gantry 101, 301. The embodiment of FIG. 4 shows a design of the waveguide 401 which may be optimized for the maximum efficiency of the MIMO system. The waveguide provides the multipath environment needed for the communication to occur in the case there is no line-of-sight connection between an antenna pair.

Figure 5:
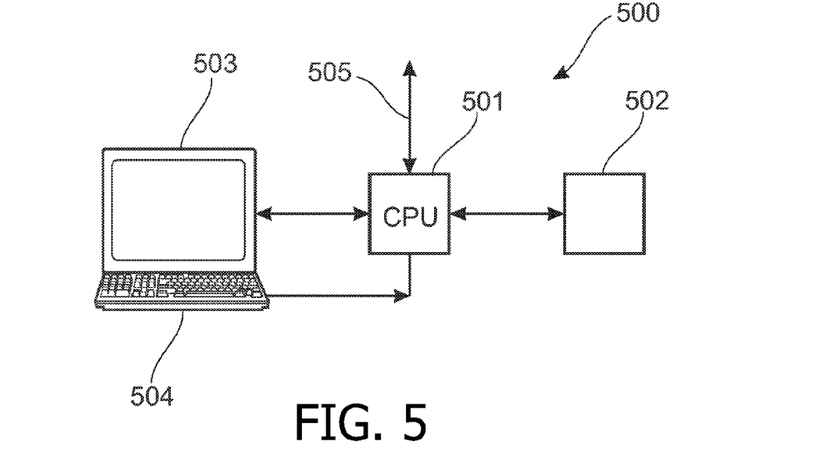
FIG. 5 shows an exemplary embodiment of a data processor to be implemented in an computed tomography apparatus.

FIG. 5 depicts an exemplary embodiment of a data processing device 500 according to the present invention for executing an exemplary embodiment of a method in accordance with the present invention.

The data processing device 500 depicted in FIG. 5 comprises a central processing unit (CPU) or image processor 501 connected to a memory 502 for storing an image depicting an object of interest, such as a patient. The data processor 501 may be connected to a plurality of input/output network or diagnosis devices, such as an MR device or a CT device. The data processor 501 may furthermore be connected to a display device 503, for example a computer monitor, for displaying information or an image computed or adapted in the data processor 501. An operator or user may interact with the data processor 501 via a keyboard 504 and/or other output devices, which are not depicted in FIG. 5. Furthermore, via the bus system 505, it is also possible to connect the image processing and control processor 501 to, for example a motion monitor, which monitors a motion of the object of interest. In case, for example, a lung of a patient is imaged, the motion sensor may be an exhalation sensor. In case the heart is imaged, the motion sensor may be an electrocardiogram (ECG).

In the following, referring to FIG. 6, a computer tomography system 600 according to an exemplary embodiment of the invention will be described.

Figure 6:
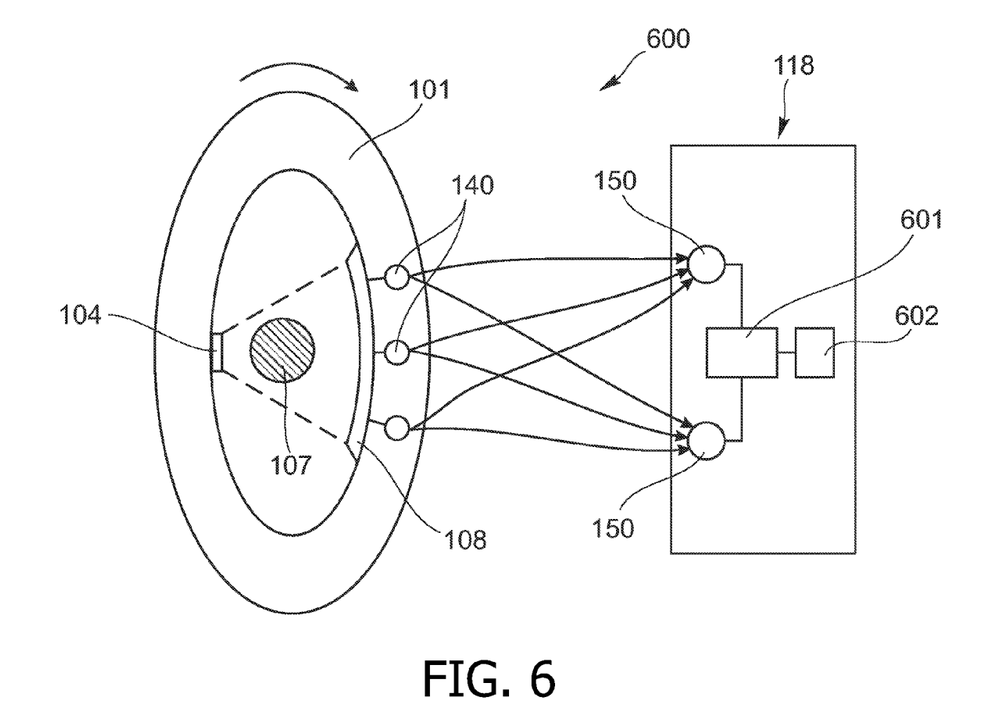
FIG. 6 shows a computed tomography apparatus according to a fifth embodiment of the invention.

In the embodiment of FIG. 6, there are provided three emitter antennas 140 and two receiver antennas 150. Each of the emitter antennas 140 emits electromagnetic radiation encoding the data detected by the detector 108.

As can be taken from FIG. 6, each of the receiver antennas 150 detects all signals coming from all emitter antennas 140. According to the MIMO system, the data are evaluated by a reconstruction unit 601 so as to provide the full data set of the detector 108 at a high bandwidth which may then be provided to an image reconstruction unit 602 for reconstructing a three-dimensional image of the object under investigation 107.

Exemplary technical fields, in which the present invention may be applied advantageously, include baggage inspection, medical applications, material testing, and material science. An improved image quality and less artefacts in combination with a low effort may be achieved. Also, the invention can be applied in the field of heart scanning to detect heart diseases.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A data processing device, comprising;
a gantry including a movable data acquisition device;
a plurality of emitter antennas arranged on the movable data acquisition device and adapted to emit electromagnetic radiation including data acquired by the movable data acquisition device;
a plurality of receiver antennas arranged on the gantry, each of the plurality of receiver antennas adapted to receive the electromagnetic radiation emitted by each of the plurality of emitter antennas; and
a data processing unit coupled to the plurality of receiver antennas and adapted to extract the data acquired by the movable data acquisition device from the electromagnetic radiation received by the plurality of receiver antennas.

2. The data processing device of claim 1,
wherein the movable data acquisition device is a rotatable data acquisition device.

3. The data processing device of claim 1,
wherein the number of emitter antennas is larger, equal or smaller than the number of receiver antennas.

4. The data processing device of claim 1,
wherein the plurality of emitter antennas, the plurality of receiver antennas and the data processing unit are designed as a multiple-input multiple-output communication system.

5. The data processing device of claim 1,
wherein the plurality of receiver antennas are adapted for a wireless two-way communication with the plurality of emitter antennas.

6. The data processing device of claim 1,
wherein at least a part of the plurality of receiver antennas are arranged spatially fixed to a stationary portion of the gantry and apart from the movable data acquisition device.

7. The data processing device of claim 1,
wherein at least a part of the plurality of receiver antennas are arranged movably on the movable data acquisition device.

8. The data processing device of claim 7,
wherein the data processing unit is coupled to the plurality of receiver antennas by means of a wired communication channel.

9. The data processing device of claim 1,
wherein the data processing unit is arranged spatially fixed and apart from the movable data acquisition device.

10. The data processing device of claim 1,
the gantry comprising a shielding element for shielding the plurality of emitter antennas and the plurality of receiver antennas with respect to the data processing unit and/or an environment.

11. The data processing device of claim 1,
wherein the plurality of receiver antennas are adapted to emit electromagnetic radiation including feedback information concerning the communication between the plurality of receiver antennas and the plurality of emitter antennas;
wherein the plurality of emitter antennas are adapted to receive the electromagnetic radiation emitted by the plurality of receiver antennas.

12. The data processing device of claim 1,
wherein a communication between the plurality of receiver antennas and the plurality of emitter antennas is bidirectional.

13. The data processing device of claim 1,
wherein a communication between the plurality of receiver antennas the plurality of emitter antennas includes estimating properties of a transmission medium.

14. The data processing device of claim 1,
wherein a communication between the plurality of receiver antennas and the plurality of emitter antennas is based on a periodic channel.

15. The data processing device of claim 1,
wherein a communication between the plurality of receiver antennas and the plurality of emitter antennas includes at least one of the group consisting of estimating a channel matrix, estimating a channel distortion, and estimating a channel equalization.

16. The data processing device of claim 1,
configured as one of the group consisting of a baggage inspection apparatus, a medical application apparatus, a material testing apparatus and a material science analysis apparatus.

17. A tomography apparatus for examination of an object of interest, the tomography apparatus comprising:
an electromagnetic radiation source adapted to emit a beam to the object of interest;
a detecting device adapted to detect the beam having passed the object of interest; and
a data processing device including:
a gantry including a movable data acquisition device,
a plurality of emitter antennas arranged on the movable data acquisition device and adapted to emit electromagnetic radiation including data acquired by the movable data acquisition device,
a plurality of receiver antennas arranged on the gantry, each of the plurality of receiver antennas adapted to receive the electromagnetic radiation emitted by each of the plurality of emitter antennas, and
a data processing unit coupled to the plurality of receiver antennas and adapted to determine structural information concerning the object of interest based on an analysis of detecting signals received from the detecting device which is coupled to the plurality of emitter antennas of the data processing device.

18. The tomography apparatus of claim 17,
adapted as one of the group consisting of a computed tomography apparatus, a positron emission tomography apparatus, and a single photon emission computed tomography apparatus.

19. The tomography apparatus of claim 17,
wherein the gantry comprises a rotatable portion on which the electromagnetic radiation source, the detecting device and the plurality of emitter antennas are mounted.

20. A method of processing data, the method comprising
emitting, by means of a plurality of emitter antennas arranged on a movable data acquisition device of a gantry, electromagnetic radiation including data acquired by the movable data acquisition device;
receiving, by means of a plurality of receiver antennas arranged on the gantry, the electromagnetic radiation emitted by each of the plurality of emitter antennas;
extracting, by means of a data processing unit coupled to the plurality of receiver antennas, the data acquired by the movable data acquisition device from the electromagnetic radiation received by the plurality of receiver antennas.

21. A computer-readable medium, in which a computer program of processing data is stored which, when being executed by a processor, is adapted to control or carry out:
emitting, by means of a plurality of emitter antennas arranged on a movable data acquisition device of a gantry, electromagnetic radiation including data acquired by the movable data acquisition device;
receiving, by means of a plurality of receiver antennas arranged on the gantry, the electromagnetic radiation emitted by each of the plurality of emitter antennas;
extracting, by means of a data processing unit coupled to the plurality of receiver antennas, the data acquired by the movable data acquisition device from the electromagnetic radiation received by the plurality of receiver antennas.

22. A program element of processing data, which program element, when being executed by a processor, is adapted to control or carry out
emitting, by means of a plurality of emitter antennas arranged on a movable data acquisition device of a gantry, electromagnetic radiation including data acquired by the movable data acquisition device;
receiving, by means of a plurality of receiver antennas arranged on the gantry, the electromagnetic radiation emitted by each of the plurality of emitter antennas;
extracting, by means of a data processing unit coupled to the plurality of receiver antennas, the data acquired by the movable data acquisition device from the electromagnetic radiation received by the plurality of receiver antennas.

23. A data processing device, comprising:
a gantry;
plurality of emitter antennas arranged on the gantry and adapted to emit electromagnetic radiation in which data are encoded;
a plurality of receiver antennas each adapted to receive the electromagnetic radiation emitted by each of the plurality of emitter antennas, wherein the plurality of receiver antennas are arranged on a movable portion of the gantry;
a data processing unit coupled to the plurality of receiver antennas and adapted to extract the data from the electromagnetic radiation received by the plurality of receiver antennas.

* * * * *